United States Patent

Marchon et al.

[11] Patent Number: 6,142,006
[45] Date of Patent: Nov. 7, 2000

[54] METHOD AND APPARATUS FOR CALIBRATING A GLIDE HEAD AND DETECTION SYSTEM FOR A MAGNETIC DISK DRIVE

[75] Inventors: Bruno Jean Marchon, Palo Alto; David Shiao-Min Kuo, Castro Valley; Wei Hsin Yao; Chiao-Ping Ku, both of Fremont, all of Calif.

[73] Assignee: Seagate Technology LLC, Scotts Valley, Calif.

[21] Appl. No.: 09/121,595

[22] Filed: Jul. 24, 1998

Related U.S. Application Data

[60] Provisional application No. 60/057,019, Jul. 25, 1997.

[51] Int. Cl.$^7$ .............................. G01B 7/34; G01B 11/30
[52] U.S. Cl. .................. 73/1.81; 250/252.1; 324/202; 356/243.3; 73/1.89
[58] Field of Search ................................... 73/1.81, 1.89; 250/252.1 A; 356/243.3, FOR 106; 324/202

[56] References Cited

U.S. PATENT DOCUMENTS

| | | | |
|---|---|---|---|
| 4,624,564 | 11/1986 | Dahlgren .............................. | 360/103 X |
| 4,828,895 | 5/1989 | Brickert et al. ........................... | 428/65 |
| 4,931,338 | 6/1990 | Toffle ...................................... | 428/65 |
| 5,453,831 | 9/1995 | Li et al. . | |
| 5,552,884 | 9/1996 | Li et al. .............................. | 356/357 X |
| 5,567,864 | 10/1996 | Coon et al. . | |
| 5,631,408 | 5/1997 | Baumgart et al. ....................... | 73/1.81 |
| 5,675,462 | 10/1997 | Ayabe .................................... | 360/135 |
| 5,689,057 | 11/1997 | Baumgart et al. . | |
| 5,689,064 | 11/1997 | Kennedy et al. ......................... | 73/105 |

Primary Examiner—Thomas P. Noland
Attorney, Agent, or Firm—McDermott, Will & Emery

[57] ABSTRACT

A method and apparatus for calibrating a glide head and detector system performs a pre-screening to ensure the quality of the glide head and the piezoelectric sensor in the detection system. The glide head and the piezoelectric sensor detect a signal when the glide head makes contact with the disk, such as a magnetic recording disk. Calibration of the detection system utilizes a specially made bump disk that has asperities of desired height and size that protrude out of a flat disk surface. The glide head is flown over the bump disk, and by gradually reducing the disk spinning velocity, the head is brought closer to the disk and eventually into contact with the asperity. The onset of contact, as detected by the piezoelectric sensor, defines a disk spinning velocity for the head to fly at the desired height. In order to decouple the glide head flying characteristics and the piezoelectric quality and transfer function from other factors that affect the calibration of the detection system, laser pulses are directed at the glide head. Head vibrations are introduced in the glide head and detected by the piezoelectric sensor. The head excitations are recorded as a spectrogram in which the resonance frequencies are observed. From the amplitude and frequency readings, head resonance frequencies are identified and the piezoelectric sensor response is characterized. This allows the pre-screening of the head/sensor system and the decoupling of the glide head flying characteristics and the piezoelectric sensor quality from the asperity integrity effects on the calibration of the detection system.

10 Claims, 5 Drawing Sheets

(1 of 5 Drawing Sheet(s) Filed in Color)

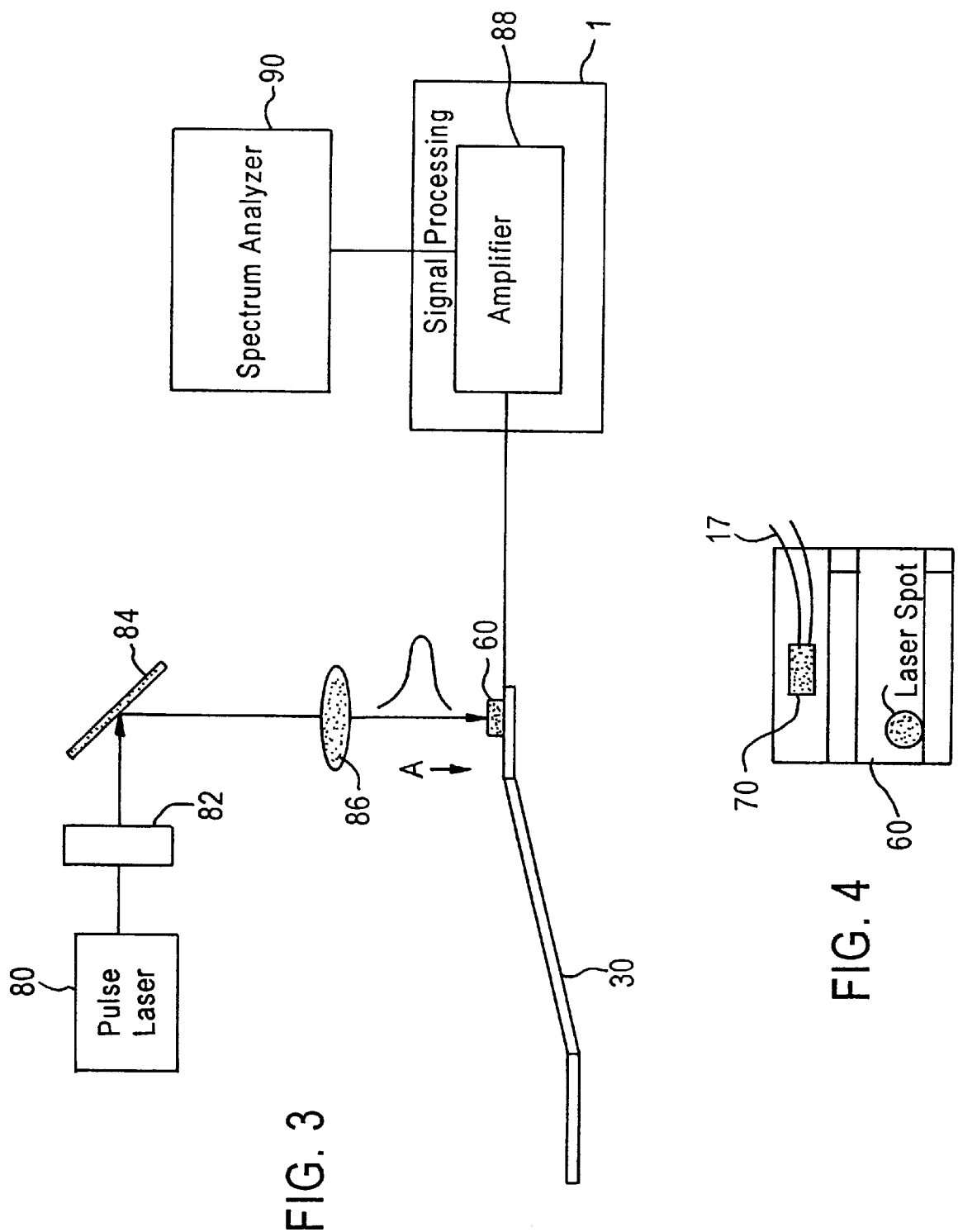

METHOD AND APPARATUS FOR CALIBRATING A GLIDE HEAD AND DETECTION SYSTEM FOR A MAGNETIC DISK DRIVE

CROSS-REFERENCE TO RELATED APPLICATIONS

This application claims priority from provisional patent application Ser. No. 60/057,019 filed Jul. 25, 1997, entitled NON-CONTACT GLIDE HEAD CALIBRATION WITH A PULSE LASER, which is incorporated herein by reference.

FIELD OF THE INVENTION

The present invention is related to the field of glide head assemblies adapted to detect asperities which project above a specified height from moving surfaces, and more particularly, to method and apparatus for calibrating the glide head and detection system.

BACKGROUND OF THE INVENTION

Hard disk drives are used in most modern computer systems to store and retrieve programs and data. The hard disks are magnetic disks which are permanently enclosed in the hard disk drive to prevent contamination. Generally, the hard disk drive includes a spindle on which the disks are mounted and rotated with a selected angular velocity. The hard disk drives include a magnetic head that is translated across the surface of the disk to allow for access to a selected annular track. The magnetic disks are typically journaled for rotation about the spindle of the hard drive in a spaced relationship to one another. A tracking arm is associated with each disk and the read/write head is mounted to this tracking arm for accessing the desired information. These magnetic heads are typically referred to as "flying" data heads because they do not contact the surface of the disk during rotation. Rather, the magnetic heads hover above the surface on an air bearing that is located between the disk and head which is caused by rotation of the disk at high speeds.

A persisting problem with rigid magnetic memory disks is that asperities, which are essentially protrusions on the surfaces of the disks, may cause an anomaly when encountered by the head during high speed revolutions. These asperities can cause errors in the transfer of information or even damage to the head. In effort to reduce the occurrences of asperities, manufacturers commonly burnish the memory surfaces of the disk to remove asperities. In the burnishing process, a burnishing head, rather than a magnetic read-write head, is mounted in a similar manner relative to the disk as discussed above. Burnishing heads may be designed as either "flying" heads which pass over the surface to be burnished or they may be designed as "contact" burnishing heads which have a contact surface that directly engages the asperities. During the burnishing process, the burnishing head operates to smooth out the surface protrusions.

The next step in further refining magnetic (or optical) disks for production is detecting any unwanted asperities which remain after the burnishing operation and is accomplished through the use of a glide head. The purpose of a glide head is to detect, via proximity or by contact, any remaining asperities which may come into contact with the write data head during use. Glide heads are, thus, required to hover and detect asperities which are located above specified data head flying heights. Glide heads dynamically test the integrity of a disk's surfaces.

The continuous trend in the magnetic media industry is towards requiring magnetic recording disks to have ever increasing recording densities. Accordingly, for manufacturers to develop production quality rigid memory disks for use in this industry and the computer industry in general, it is necessary to utilize glide heads that have more sensitive response characteristics. Existing glide heads have inherent problems associated with them because it is difficult to precisely control the electrical response characteristics of these devices.

The electrical response of a glide head is dependent upon detection parameters of amplitude, frequency, and signal to noise ratio (S/N). However, because the industry's demands for higher magnetic densities requires a lowering of the data head's flying height over the surface of the magnetic disks, it becomes more difficult to tighten the physical tolerances of glide heads and effectively control the frequency, amplitude and signal to noise ratio. Current glide head designs, for example, rely predominantly on the function of an accelerometer to control these detection parameters. Unfortunately, these designs are becoming less effective at detecting asperities as demands increase and they are increasingly susceptible to physical and thermal stresses during shipping and use.

In the past, it has been known to employ a glide head, whose slide component is that portion of the glide head which directly contacts the surface asperities, that is configured to include a lateral wing portion that has a layer of piezoelectric material adhered thereto. As the slider comes into contact with a surface asperity, it leads to an excitation of all the natural internal vibrations of the glide head/PZT assembly. The particular disturbances of the PZT sensor causes a voltage output from the crystalline lattice of the piezoelectric material. Part of this electrical signal, in the frequency window of the electronic filter in use, is then monitored as an r.m.s (root-mean-square) value. Typically, one sets a threshold r.m.s voltage over which discs are rejected for improper surface finish. The problem is that since all glide heads are manufactured with a certain geometric tolerance, they all have a different transfer function, i.e., they all respond differently in both frequency and amplitude to a given impact asperity. It is therefore critical to calibrate precisely the response of each individual glide head.

The current glide technology uses the glide head and piezoelectric sensor to detect a signal upon head-disk contact. The detection system is traditionally calibrated by utilizing a specially made "bump disk" which has asperities of desired height and size that protrude out of a flat disk surface. The asperities are either deposited via sputtering techniques or formed by laser texturing techniques, for example. A glide head is then flown over the bump disk. By gradual reduction of the disk spinning velocity, the glide head is brought closer to the disk and eventually comes into contact with the asperity. The onset of contact, as detected by the piezoelectric sensor, defines the specific disk spinning velocity for the head to fly at the desired height.

One of the problems with this calibration technique, however, is that the calibration may be affected by a number of different factors. These include the asperity integrity, the glide head flying characteristics, the quality of the piezoelectric sensor, and the transfer function. The combined effects of these different factors are complex and extremely difficult to decouple.

SUMMARY OF THE INVENTION

There is a need for a method and apparatus that ensures the quality of the glide head and the piezoelectric sensor so that any effects on the calibration of the detection system due to the quality of the glide head and piezoelectric sensor may be accounted for during the calibration process.

This and other needs are met by embodiments of the present invention which provide an arrangement for calibrating a glide head and detector system comprising a radiant energy generator and means for calibrating the glide head and detector system with radiant energy generated by the radiant energy generator. In certain embodiments, the radiant energy generator is a pulse laser that produces laser pulses. These laser pulses are focused by a pulse laser delivery system onto a surface of the glide head. The laser pulses excite the glide head at glide head excitation frequencies. The controlled laser pulses impinge upon the glide head either by thermal shock or by photon pressure shock, to introduce vibrations in the glide head. These vibrations can be detected by a piezoelectric sensor. The arrangement of the glide head and detector can be characterized easily and precisely, as the input excitations are extremely controllable by this arrangement. This provides the advantage of eliminating uncertainties introduced by the current calibration technique and can be used to pre-screen the glide head and detector system. Once the head resonance frequencies are identified and the piezoelectric sensor response is characterized, these factors can be filtered or compensated for when the detection system is calibrated.

The earlier stated needs are also met by another embodiment of the present invention which provides a method of calibrating a detection system for detecting the contact of a glide head with a recording media surface. The method comprises the steps of directing a laser beam to impinge on a surface of a glide head. A response to the glide head to the impingement of the laser beam is then measured. A calibration characteristic of the glide head is then determined based upon the measured response.

One of the advantages of the method of the present invention is that the technique to pre-screen the quality of the glide head in the piezoelectric sensor is a non-contact method and is non-intrusive to the glide head. By using an excitation that is extremely controllable, the head/sensor system is characterized easily and precisely to eliminate the uncertainties introduced by the combined effects of asperity integrity, glide head flying characteristics and piezoelectric sensor quality and transfer function.

Additional features and advantages of the present invention will become readily apparent to those skilled in this art from the following detailed description, wherein embodiments of the invention are described, simply by way of illustration of the best mode contemplated for carrying out the invention. As will be realized, the invention is capable of other and different embodiments, and several details are capable of modifications and various obvious respects, all without departing from the invention. Accordingly, the drawings and description are to be regarded as illustrative in nature, and not as restrictive.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 3 is a schematic block diagram of an arrangement to calibrate a glide head in a non-contact manner in accordance with embodiments of the present invention.

FIG. 4 is a depiction of a glide head as viewed in the direction of arrow A of FIG. 3.

DETAILED DESCRIPTION OF EXEMPLARY EMBODIMENTS

The present invention broadly relates to the calibration of a system to detect signals upon contact between a flying head and a data recording disk. Typically, current glide technology involves the use of a glide head and piezoelectric sensor that detects the signal upon head-disc contact. The traditional calibration of the detection system utilizes a specially made "bump disk" which has asperities of desired height and size that protrude out of the flat disk surface. The onset of head-disk contact, as detected by the piezoelectric sensor, defines the specific disk spinning velocity for the head to fly at the desired height. The calibration technique is affected by a number of factors, including the flying characteristics of the glide head and the quality and transfer function of the piezoelectric sensor. The present invention calibrates the glide head in a non-contact manner so that the glide head and piezoelectric sensor response can be characterized and decoupled from the calibration of the detection system.

Figure 1:
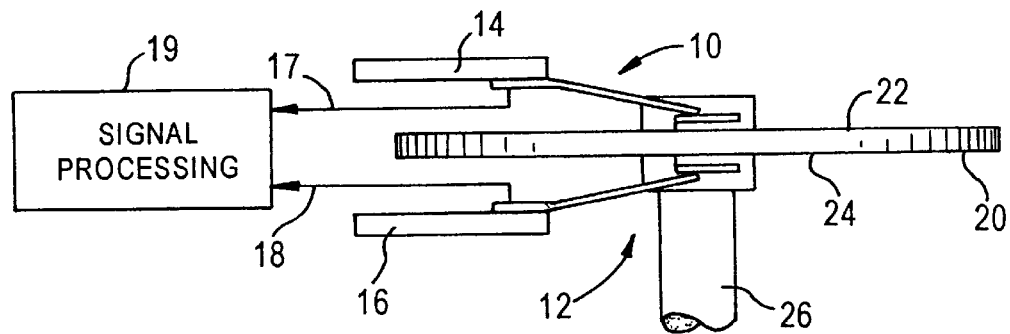
FIG. 1 is a diagrammatic side view of a pair of glide head assemblies in accordance with the prior art and depicting the glide head assemblies in use to detect the presence of asperities on opposite moving surfaces of a magnetic disk.

FIG. 1 depicts an exemplary arrangement of a pair of glide head assemblies 10 and 12 that are used in detecting the presence of asperities on opposite surfaces of a rigid magnetic memory disk 20 that is journaled for rotation about spindle 26. While FIG. 1 only depicts a detection apparatus associated with a single rigid memory disk 20, it should be appreciated that a plurality of rigid memory disks could be rotatably journaled about spindle 26 with each of these memory disks having an associated pair of glide head assemblies.

The arrangement of FIG. 1 is exemplary only to depict one arrangement to explain the operation of the present invention to such an arrangement. The present invention, however, is applicable for calibrating other arrangements and configurations of glide heads and detection systems. As shown in FIG. 1, each of the glide head assemblies 10 and 12 has an associated support structure and is adapted for use with a system for testing one of the moving surfaces of rigid memory disk 20. Specifically, an upper glide head assembly 10 is employed to detect the presence of asperities on an upper surface 22 of the rigid memory disk 20. Upper glide head assembly 10 is mounted to a support structure 14 and communicates the detection results, via electrical lead 17, to a system that includes signal processing circuit 19. The signal processing circuit 19 includes standard monitoring circuitry as known in the art with filtering circuitry capable of selecting a desired bandwidth for monitoring. Similarly, a lower glide head assembly 12 is employed to detect the presence of asperities on a lower surface 24 of rigid memory disk 20. Lower glide head assembly 12 is mounted to a lower support structure 16 and communicates detection results, via electrical leads 18, to signal processing circuit 19.

Figure 2:
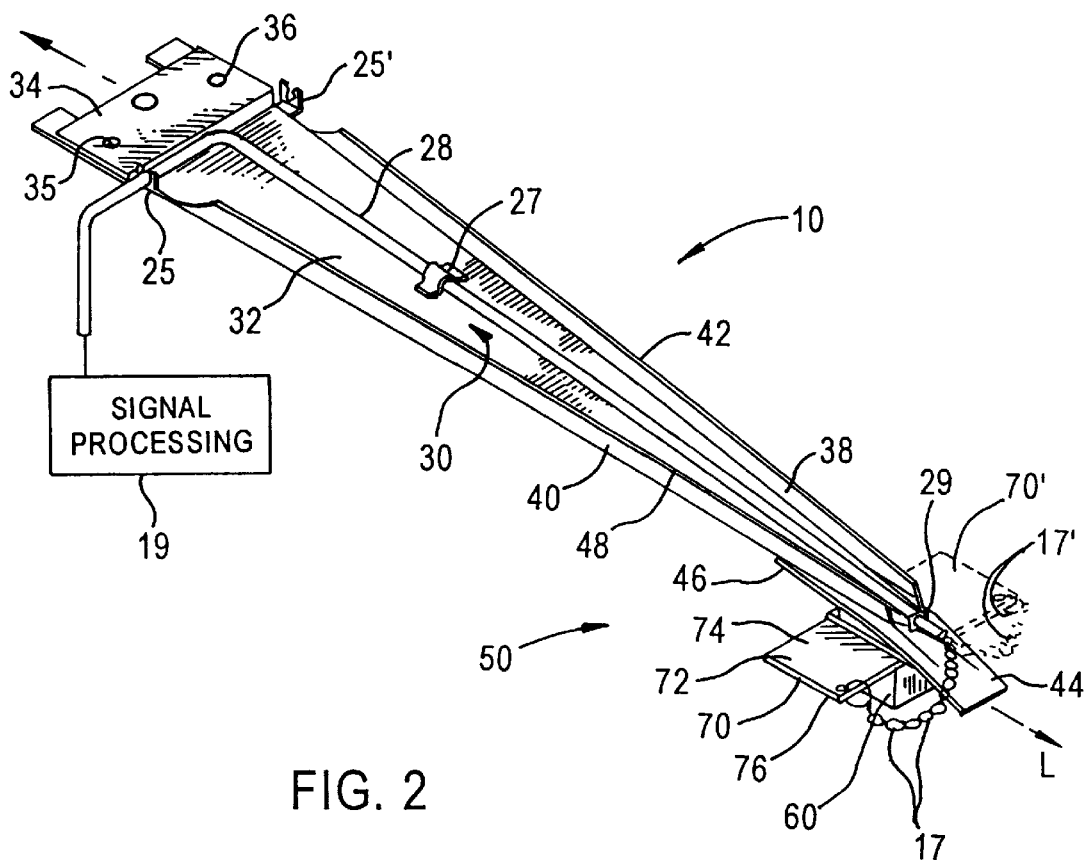
FIG. 2 is a perspective view of the construction of the upper glide head assembly represented in FIG. 1 and showing, in phantom, an alternative position for the piezoelectric transducer as it would be located for a lower guide head assembly in FIG. 1.

In FIG. 2, the representative upper glide head assembly 10 comprises a flexure 30 and glide head structure 50. Flexure 30 includes a proximal end portion 32 which is adapted to be mounted to the support structure 14 in FIG. 1 by a mounting bracket 34 that is provided with a pair of spaced apart securement holes 35 and 36. A distal end portion 38 of flexure 30 is adapted to be positioned in proximity to the upper moving surface 22 of rigid memory disk 20. Flexure 30 extends along a longitudinal axis "L" and includes a pair of spaced apart, upstanding side walls 40, 42 which are symmetrical about longitudinal axis "L" and converge from proximal end 32 toward distal end 38. Flexure 30 also includes a tongue 44 which is mounted to the flexure 30 and forms a distal end portion 38.

As also shown in FIG. 2, the glide head structure 50 of upper glide head assembly 10 broadly includes a slider 60 that projects downwardly from a lower surface 46 of flexure 30 and a piezoelectric transducer 70 which is partly sandwiched between slider 60 and tongue 44. Piezoelectric transducer 70 is configured as a flat plate and has an exposed free end portion 72 which projects outwardly from an outer region between distal end portion 38 and slider 60 to define a cantilever having a selected length "d" and a selected width "w". The exposed free end portion 72 projects laterally of distal end portion 38.

A pair of electrical leads 17 are respectively connected to the upper and lower surfaces 74 and 76 of piezoelectric transducer 70. Layers of gold conducting material may be provided for these connections. The electrical lead 17 operates to communicate electrical signals to signal processing unit 19. A sleeve 28 is disposed longitudinally along an upper surface 48 of flexure 30 and this sleeve 28 operates to receive and support electrical lead 17. A pair of mounting U-brackets 25 and bracket 29 are, respectively, affixed to the proximal end portion 32 and the distal end portion 38 of flexure 30 for this purpose. In addition, bracket 27 is also provided on the upper surface 48 to help receivably retain sleeve 28 so that the integrity of electrical signals produced by upper glide head assembly 10 is not jeopardized by any unnecessary movement of electrical leads 17 during operation.

It should also be appreciated from FIG. 2 that the constructions of lower glide head assembly 12 would be identical to that described herein with reference to upper glide assembly 10 with the exception that the piezoelectric transducer 70' associated with lower glide head assembly 12 would extend laterally outwardly from an opposite side of flexure 30 and that the electrical lead 17' which is associated therewith could be supported by U-bracket 25' positioned at the proximal end end portion 32 of flexure 30.

In operation, an asperity on the surface 22 of the disk 20 will contact a slider 60 so that it is urged upwardly. This disturbance results in a compressive force being exerted on a portion of the piezoelectric transducer 70. This compressive force disturbs the crystalline lattice of piezoelectric transducer 70 thereby causing an electrical signal to be generated in an electrical lead 17, these signals being communicated back to the signal processing unit 19. However, it should also be appreciated that a variety of other electronic signals are also generated by virtue of the detection of an asperity. For example, the disturbance causes the forced vibration within flexure 30 and generates an appreciable amount of noise in the system. These signals dampen fairly rapidly. More importantly, though, the disturbance also results in the generation of an electronic signal by virtue of the cantilevered orientation of piezoelectric transducer 70 which acts as a moment arm and begins to vibrate at a dominant amplitude in frequency. Each of the various electronic signals, which have different frequency and amplitude characteristics, are communicated to the signal processing unit 19 where an appropriate bandpass filter may be applied to select the dominant mode.

In the prior art, the specific characteristics and vibration frequencies of the glide head, as well as the quality of the piezoelectric sensor and its transfer function, were not known for individual glide head/sensor systems. In certain known arrangements, the performance characteristics of the glide head assembly may be varied by altering the dimensional parameters of the individual components of the assembly. However, the testing and calibration of the characteristics and quality and transfer function of the glide head and the piezoelectric sensor has been difficult to decouple from the other factors, such as the asperity integrity.

An arrangement for calibrating a glide head and detector system in accordance with the embodiments of the present invention is depicted in FIG. 3. This arrangement may be employed to calibrate glide head and detector systems of different configurations, not just the particular exemplary configuration depicted in FIGS. 1 and 2. The arrangement of the present invention does not replace the current technique of calibrating a detection system using a specially made bump disk having asperities that protrude out of the flat disk surface. Instead, the present invention enhances such a technique by providing a pre-screening that ensures the quality of the glide head and the piezoelectric sensor. As will be seen, this pre-screening is non-contact in nature, and is also non-intrusive to the glide head.

The present invention pre-screens the glide head in the piezoelectric sensor by using controlled laser pulses directed to impinge upon the head-sensor system. A pulse laser 80 generates radiant energy in the form of laser pulses. An exemplary pulse laser is a Nd-YVO$_4$ type pulse laser, although other types of lasers may be used, or other radiant energy generators may also be used in the present invention without departing from the scope of the invention.

Exemplary values for the laser pulses are 0.1–0.2 $\mu$J of power, with laser pulse durations of 30 ns, at a frequency of 1.064 microns. However, these values should be considered exemplary only, as other laser parameters may be used to calibrate the glide head and detector system, as will be appreciated by those of skill in the art.

The laser pulses are attenuated by an attenuator 82 and reflected off a mirror 84 to a focusing lens 86. With proper selection and positioning of lens 86, as known to those skilled in the art, the laser pulses may be sized and directed to impinge upon any given location of the glide head 60. When the laser pulses impinge upon the glide head 60, either by thermal shock or photon pressure shock, vibrations in the glide head 60 are introduced. The crystalline lattice of the piezoelectric transducer 70 is disturbed, causing an electronic signal to be generated in the electrical leads 17. These signals are communicated to an amplifier 88 in the signal processing unit 19.

Figure 5:
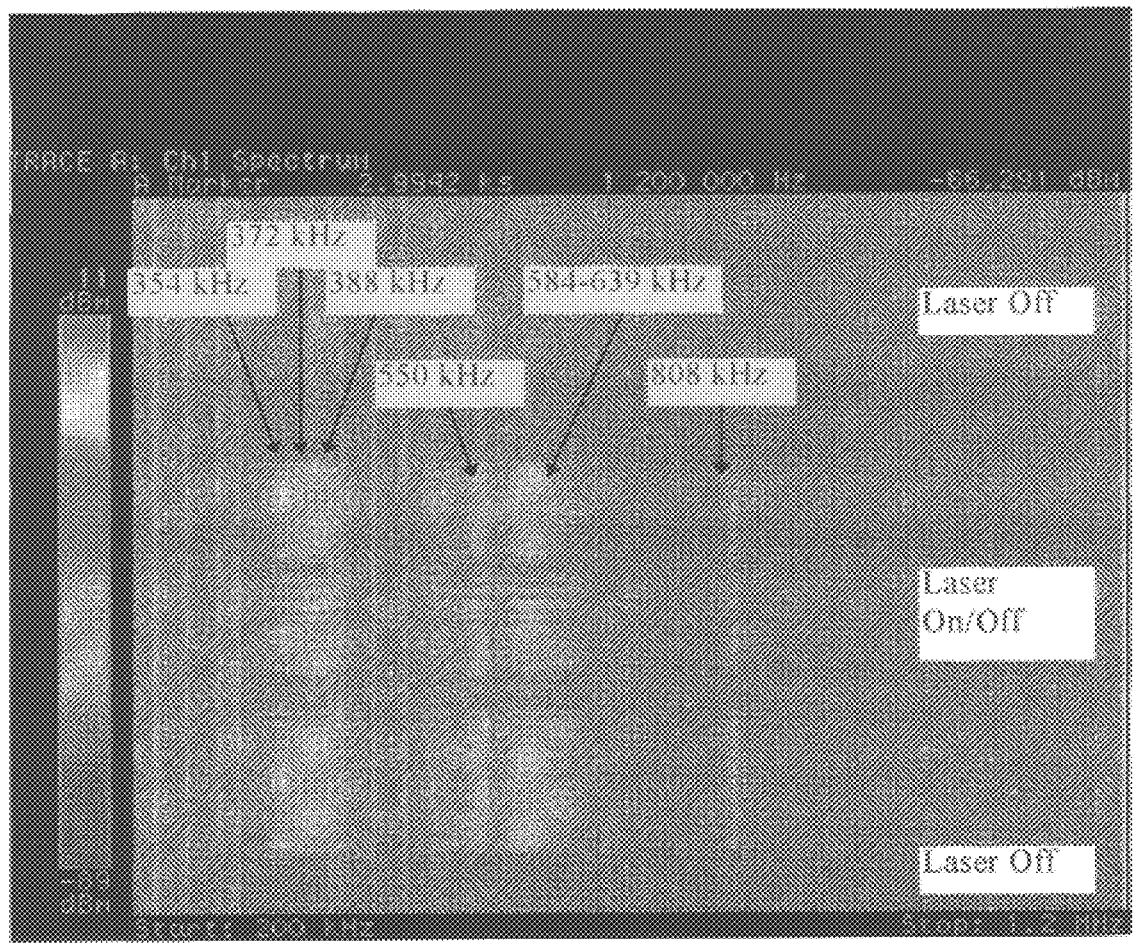
FIG. 5 is an exemplary frequency pattern of head excitations recorded as a spectrogram in which the vertical axis represents time and the horizontal axis represents frequency.

The input excitation is extremely controllable by controlling the output of the pulse laser 80. Hence, the glide head and piezoelectric sensor system can be characterized easily and precisely. This allows some uncertainties introduced by current calibration techniques to be eliminated, while also pre-screening the head and sensor system. A spectrum analyzer 90 receives the signals from the amplifier 88 in the signal processing unit 19. A suitable spectrum analyzer 90 is an HP89410A spectrum analyzer produced by Hewlett Packard, of Palo Alto, Calif. The spectrogram produced by the spectrum analyzer 90 records the head excitations with a vertical axis representing time and a horizontal axis representing frequency. An exemplary spectrogram produced by spectrum analyzer 90 is depicted in FIG. 5. In this figure, when the laser 80 is turned on so that the laser pulses impinge upon the glide head 60, (see FIG. 4, for example), several head excitation frequencies that correspond to slider body resonance frequencies are observed. The excitation frequencies disappear when the laser 80 is turned off and reappear when the laser 80 is turned on. The pattern of head excitation frequencies is very repeatable. From these amplitude and frequency readings produced in the spectrogram, the head resonance frequencies are identified very precisely and the piezoelectric sensor response can be suitably characterized by those skilled in the art.

Figure 6A:
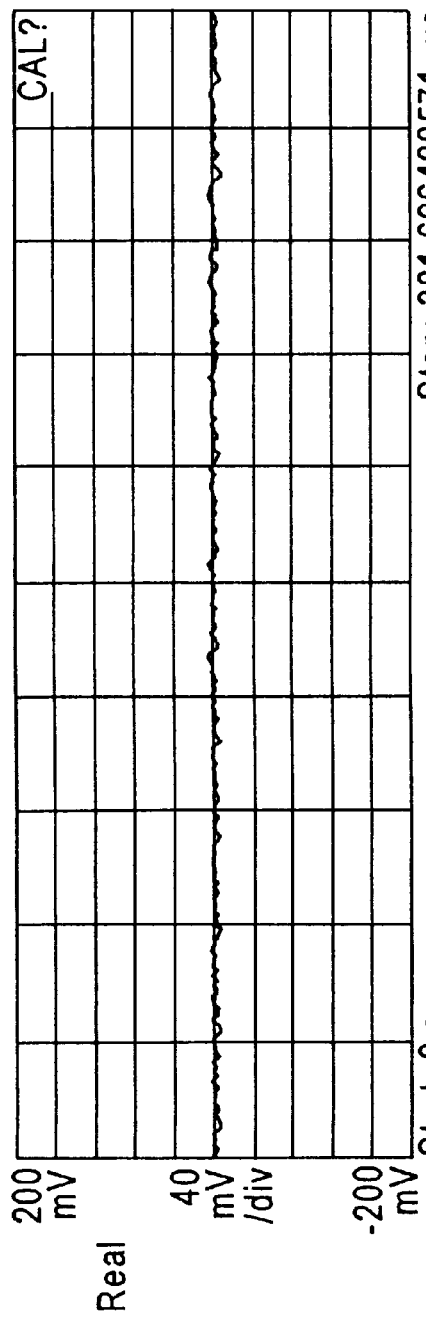
FIGS. 6A, 6B, 7A and 7B are exemplary time and frequency patterns of a head signal without and with laser pulse impingement.
Figure 6B:
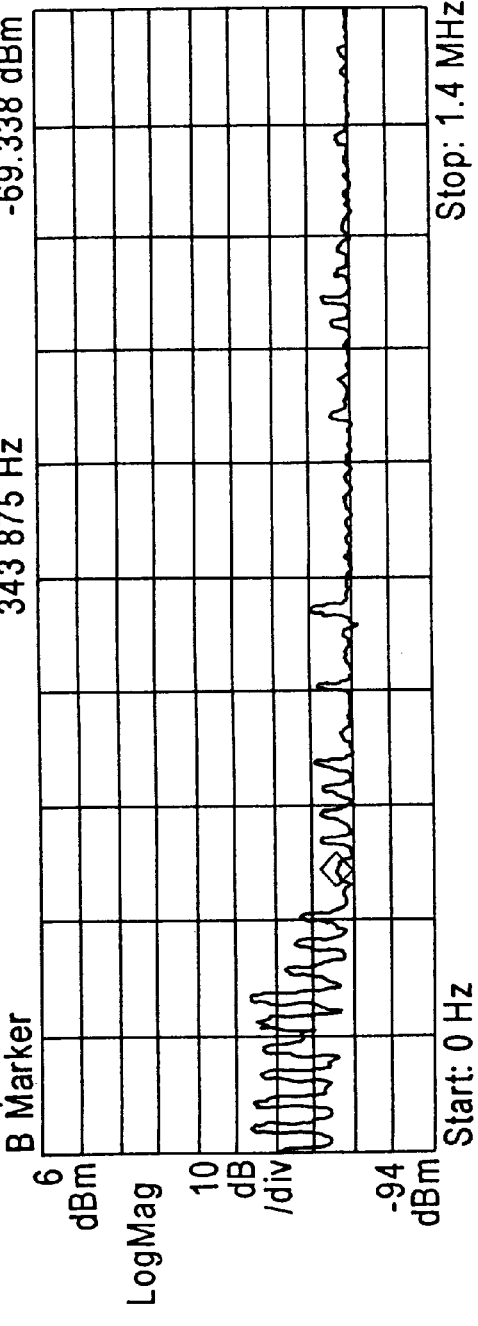
Figure 7A:
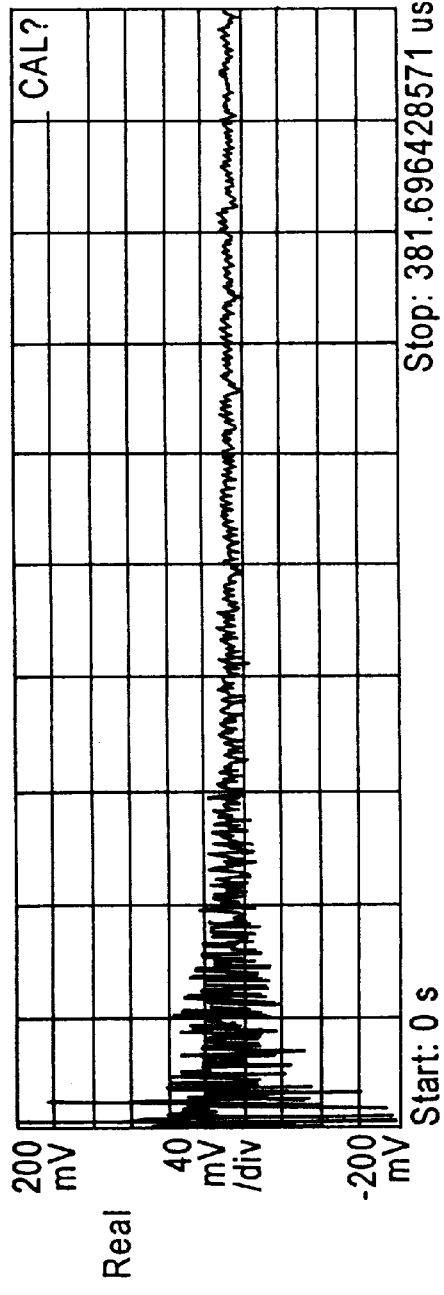
Figure 7B:
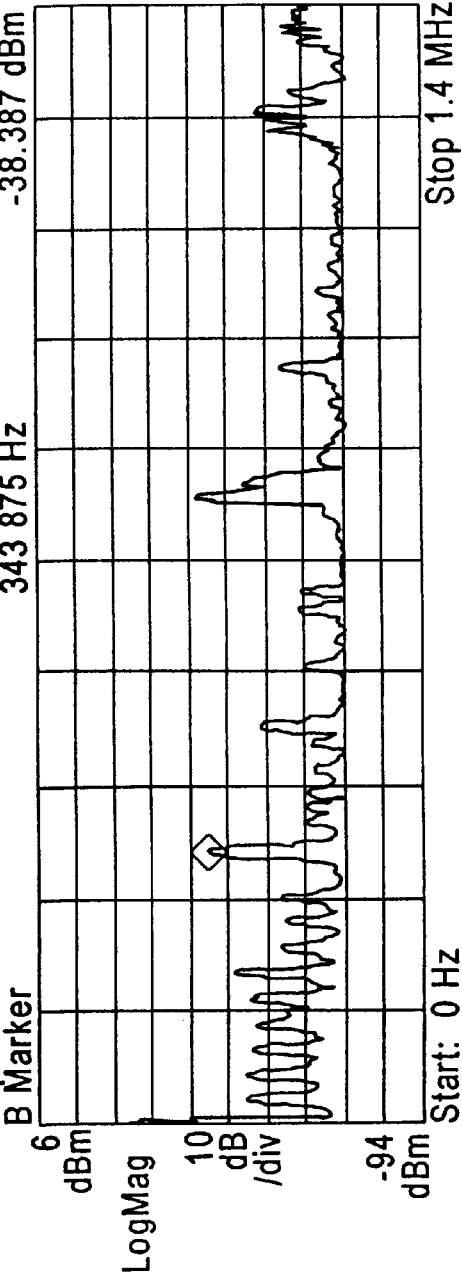

FIG. 6 depicts the time and frequency pattern of the head signal without laser excitation. FIG. 7 depicts the time and frequency pattern of the head signal with laser excitement. These patterns are exemplary only, however, as a different head will produce different patterns, as recognized in the present invention.

Once the head resonance frequencies are identified and the piezoelectric sensor response characterized, in accordance with the present invention, these effects may be compensated for (e.g. filtered) in the calibration of the detection system when the glide head is flown over the bump disk. In other words, since the glide head flying characteristics and the piezoelectric sensor quality sensor and function are known, the calibration of the detection system will depend only upon the asperity integrity. Hence, the glide head flying characteristics and the piezoelectric sensor quality and transfer function have been decoupled from the calibration detection system. With the present invention, the pre-screening technique that ensures the quality of the glide head and the piezoelectric sensor is non-contact and non-intrusive to the head, while allowing the head/sensor system to be characterized easily and precisely.

Only a preferred embodiment of the invention and but a few examples of its versatility have been shown and described in the present disclosure. It is to be understood that the present invention is capable of use in various other combinations and environments and is capable of changes and modifications within the scope of the inventive concept as expressed herein.

What is claimed is:

1. An arrangement for calibrating a glide head and detector system, comprising:

a radiant energy generator; and means for calibrating the glide head and detector system by physically exciting the glide head at glide head excitation frequencies with radiant energy generated by the radiant energy generator.

2. The arrangement of claim 1, wherein the radiant energy generator is a pulse laser that generates laser pulses.

3. The arrangement of claim 2, wherein the means for calibrating includes a pulse laser delivery system that focuses the laser pulses on a surface of the glide head.

4. The arrangement of claim 3, wherein the glide head and detector system comprises a detector and wherein the means for calibrating includes a spectrum analyzer that analyzes the glide head excitation frequencies and generates a spectrogram that is characteristic of a response of the detector.

5. The arrangement of claim 4, wherein the detector is a piezoelectric sensor.

6. An apparatus for calibrating a glide head and detector system, comprising:

a detector system coupled to the glide head to detect and measure glide head vibrations; and a radiant energy generator configured to focus sufficient radiant energy on the glide head to controllably vibrate the glide head.

7. The apparatus of claim 6, wherein the radiant energy generator is a pulse laser.

8. The apparatus of claim 7, wherein the pulse laser generates laser pulses for a duration of approximately 30 nanoseconds at a frequency of 1.064 microns.

9. The apparatus of claim 6, wherein the detector system includes a spectrum analyzer.

10. The apparatus of claim 6, wherein the detector system comprises a piezoelectric sensor mechanically coupled to the glide head and electrically coupled to a spectrum analyzer.

* * * * *